United States Patent
Bernardon

(10) Patent No.: US 6,825,360 B1
(45) Date of Patent: Nov. 30, 2004

(54) BICYCLIC AROMATIC COMPOUNDS

(75) Inventor: Jean-Michel Bernardon, Le Rouret (FR)

(73) Assignee: Galderma Research & Development S.N.C., Valbonne (FR)

( * ) Notice: Subject to any disclaimer, the term of this patent is extended or adjusted under 35 U.S.C. 154(b) by 0 days.

(21) Appl. No.: 09/619,584

(22) Filed: Jul. 19, 2000

Related U.S. Application Data

(62) Division of application No. 08/952,804, filed as application No. PCT/FR97/00391 on Mar. 5, 1997, now Pat. No. 6,147,255.

(30) Foreign Application Priority Data

Mar. 14, 1996 (FR) .............................. 96 03235

(51) Int. Cl.⁷ .................... C07D 333/24; C07D 333/08; C07D 317/00
(52) U.S. Cl. ............... 549/79; 549/79; 549/80; 549/428
(58) Field of Search ............. 549/79, 80, 429, 549/400

(56) References Cited

U.S. PATENT DOCUMENTS

| | | | |
|---|---|---|---|
| 4,650,813 A | * 3/1987 | Kooda et al. | 514/701 |
| 4,792,567 A | 12/1988 | Burkart et al. | |
| 5,763,487 A | 6/1998 | Bernardon | |
| 5,766,610 A | 6/1998 | Bernardon | |
| 5,801,253 A | * 9/1998 | Klaus et al. | 549/79 |
| 5,814,651 A | * 9/1998 | Duplantier et al. | 514/394 |
| 5,994,379 A | * 11/1999 | Bayly et al. | 514/367 |
| 6,147,255 A | * 11/2000 | Bernardon | 562/492 |
| 6,268,354 B1 | * 7/2001 | Nishimura et al. | 514/110 |
| 6,413,947 B1 | * 7/2002 | Shiraishi et al. | 514/110 |
| 6,515,021 B1 | * 2/2003 | Bernardon | 514/557 |

FOREIGN PATENT DOCUMENTS

| | | |
|---|---|---|
| EP | 0 260 162 | 3/1988 |
| EP | 260162 | * 3/1988 |
| EP | 0 679 630 A | 11/1995 |
| EP | 0 722 928 | 7/1996 |

OTHER PUBLICATIONS

Apfel et al. (CA 124:105640, abstract of J. Biol. Chem, (1995), 270(51), 30765–72).*
Obushak, N. D. et al. (DN 113:152173, CAPLUS; abstract of Zh. Org. Khim. (1990), 26(4), 873–80).*
Krutosikova, A. et al. (DN 84:58390, CAPLUS, abstract of Collect. Czech. Chem. Commun. (1975), 40(11), 3362–9).*
Chemical Abstracts, vol. 80, No. 7, Feb. 18, 1974, XP002020611.
Chemical Abstracts, vol. 80; No 19, May 13, 1974, XP002020612.
Chemical Abstracts, vol. 108, No. 4, 1975, XP002020610 (in German).
English translation of EP 0 260 162.

* cited by examiner

*Primary Examiner*—Sabiha Qazi
(74) *Attorney, Agent, or Firm*—Burns, Doane, Swecker & Mathis, L.L.P.

(57) ABSTRACT

The invention relates to novel bicyclic aromatic compounds which have the general formula (I):

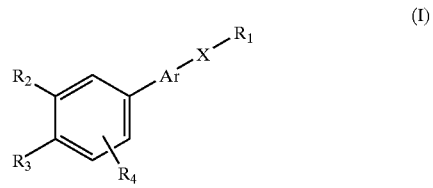

as well as to the use of these compounds in pharmaceutical compositions intended for use in human or veterinary medicine (dermatological, rheumatic, respiratory, cardiovascular and ophthalmological complaints in particular), or alternatively in cosmetic compositions.

12 Claims, 1 Drawing Sheet

BICYCLIC AROMATIC COMPOUNDS

This application is a divisional of application Ser. No. 08/952,804, filed Jan. 26, 1998 now U.S. Pat. No. 6,147,255 which is a 371 of PCT/FR97/00391 filed Mar. 5, 1997.

BRIEF SUMMARY OF THE INVENTION

The invention relates to bicyclic aromatic compounds as novel and useful industrial products. It also relates to the use of these novel compounds in pharmaceutical compositions intended for use in human or veterinary medicine, or alternatively in cosmetic compositions.

The compounds according to the invention have pronounced activity in the fields of cell differentiation and cell proliferation, and find applications more particularly in the topical and systemic treatment of dermatological complaints associated with a disorder of keratinization, dermatological (or other) complaints with an inflammatory and/or immunoallergic component, and dermal or epidermal proliferations, these being either benign or malignant. These compounds may also be used in the treatment of degenerative diseases of connective tissue, for combating both light-induced and chronological ageing of the skin and for treating disorders of cicatrization. They moreover find an application in the ophthalmological field, in particular in the treatment of corneopathies.

The compounds according to the invention may also be used in cosmetic compositions for body and hair hygiene.

Figures 1A, 1B:
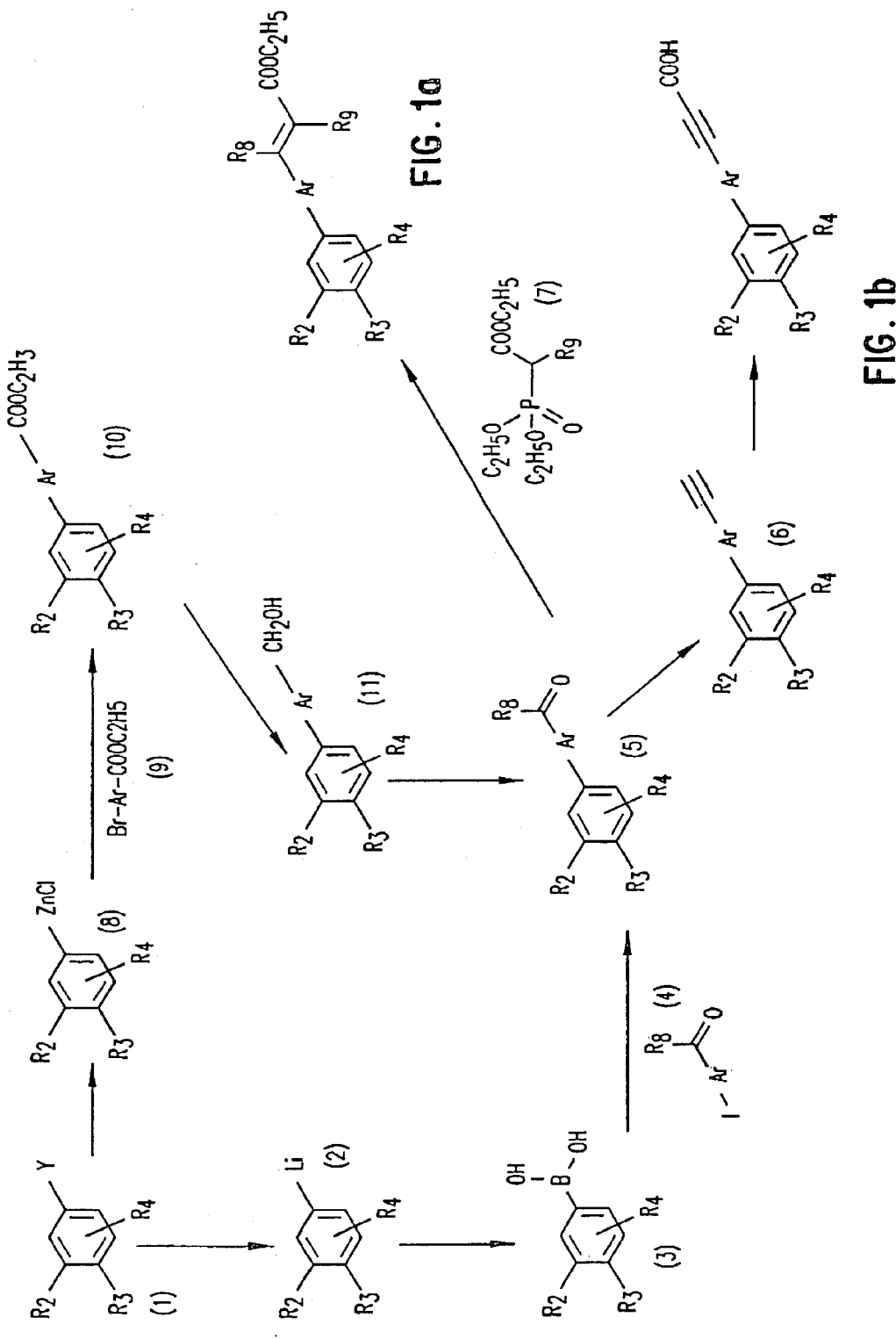
FIGS. 1a and 1b schematically depict a reaction scheme for synthesis of compounds according to the invention.

The compounds according to the invention may be represented by the general formula (I) below;

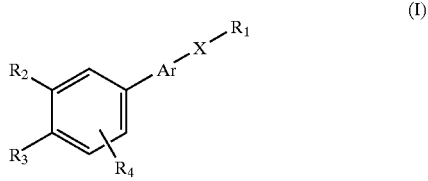
(I)

in which:

$R_1$ represents
 (i) the —$CH_3$ radical
 (ii) the radical —$CH_2OR_5$
 (iii) the radical —$COR_6$
 $R_5$ and $R_6$ having the meaning given below Ar represents a radical chosen from the radicals of formulae (a)–(e) below:

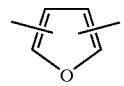
(a)

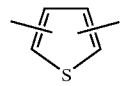
(b)

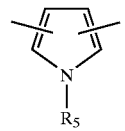
(c)

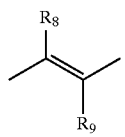
(d)

(e)

$R_5$ and $R_7$ having the meaning given below, x represents

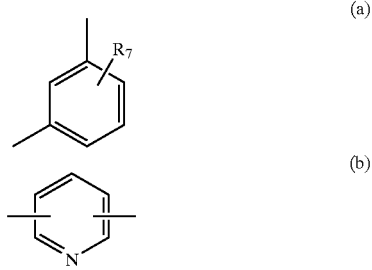

or $R_8$ and $R_9$ having the meanings given below $R_2$ and $R_3$, which may be identical or different, represent
 (i) a hydrogen atom,
 (ii) an alkyl radical having at least 3 carbon atoms, among which the carbon attached to the phenyl radical it substituted with at least two carbon atoms,
 (iii) a radical —$OR_5$,
 (iv) a radical —$SR_5$,
 $R_5$ having the meaning given below, it being understood that $R_2$ and $R_3$, taken together, may form with the adjacent aromatic ring a 5- or 6-membered ring optionally substituted with methyl groups and/or optionally interrupted by an oxygen or sulphur atom, and it being understood that $R_2$ and $R_3$ cannot at the same time have the meanings (i), (iii) and (iv) mentioned above, $R_4$ and $R_7$, which may be identical or different, represent a hydrogen atom, a halogen atom, a linear or branched alkyl radical having from 1 to 20 carbon atoms or a radical —$OR_5$, $R_5$ represents a hydrogen atom, a lower alkyl radical or a radical —$COR_{10}$ $R_{10}$ having the meaning given below, $R_6$ represents:
 (a) a hydrogen atom
 (b) a lower alkyl radical
 (c) a radical of formula:

R' and R" having the meaning given below, (d) a radical —$OR_{11}$ $R_{11}$ having the meaning given below, $R_8$ and $R_9$, which may be identical or different, represent a hydrogen atom or a lower alkyl radical, $R_{10}$ represents a lower alkyl radical, $R_{11}$ represents a hydrogen atom, a linear or branched alkyl radical having from 1 to 20 carbon atoms, an alkenyl radical, a mono- or polyhydroxyalkyl radical, an optionally substituted aryl or aralkyl radical, a sugar residue or an amino acid or peptide residue, R' and R", which may be identical or different, represent a hydrogen atom, a lower alkyl radical, a mono- or polyhydroxyalkyl radical, an optionally substituted aryl radical or an amino acid or sugar residue, or alternatively, taken together form a heterocycle.

The invention is also directed towards the salts of the compounds of formula (I) when $R_1$ represents a carboxylic acid function and the geometrical and optical isomers of the said compounds of formula (I).

When the compounds according to the invention are in the form of salts, they are preferably salts of an alkali metal or alkaline-earth metal, or alternatively of zinc or of an organic amine.

According to the present invention, the term lower alkyl radical is understood to refer to a radical having from 1 to 12, preferably from 1 to 9, carbon atoms, advantageously the methyl, ethyl, propyl, isopropyl, butyl, tert-butyl, pentyl, hexyl, heptyl, nonyl, decyl and dodecyl radicals.

The expression linear alkyl radical having from 1 to 20 carbon atoms is understood to refer in particular to the methyl, ethyl, propyl, pentyl, hexyl, octyl, decyl, dodecyl, hexadecyl and octadecyl radicals.

The expression branched alkyl radical having from 1 to 20 carbon atoms is understood to refer in particular to the 2-ethylhexyl, 2-methylbutyl, 2-methylpentyl, 1-methylhexyl and 3-methylheptyl radicals.

Among the alkyl radicals having at least 3 carbon atoms, where the carbon attached to the phenyl radical is substituted with at least two carbon atoms, mention may be made of the tert-butyl, isopropyl, 1,1-dimethylhexyl and 1,1-dimethyldecyl radical. Preferably, these radicals have not more than 20 carbon atoms, even more preferably not more than 12 carbon atoms. Advantageously, the radical (ii) is the tert-butyl radical.

Among the monohydroxyalkyl radicals, a radical having 2 or 3 carbon atoms, in particular a 2-hydroxyethyl, 2-hydroxypropyl or 3-hydroxypropyl radical, in preferred.

Among the polyhydroxyalkyl radicals, a radical having from 3 to 6 carbon atoms and from 2 to 5 hydroxyl groups, such as the 2,3-dihydroxypropyl, 2,3,4-trihydroxybutyl or 2,3,4,5-tetrahydroxypentyl radicals or the pentaerythritol residue, is preferred.

Among the aryl radicals, a phenyl radical optionally substituted with at least one halogen atom, a hydroxyl or a nitro function is preferred.

Among the aralkyl radicals, the benzyl or phenethyl radical optionally substituted with at least one halogen atom, a hydroxyl or a nitro function is preferred.

Among the alkenyl radicals, a radical containing from 2 to 5 carbon atoms and having one or more ethylenic unsaturations, more particularly such as the allyl radical, is preferred.

The term sugar residue is understood to refer to a residue derived in particular from glucose, galactose or mannose, or alternatively from glucuronic acid.

The term amino acid residue is understood to refer in particular to a residue derived from lysine, from glycine or from aspartic acid, and the term peptide residue is understood to refer more particularly to a dipeptide or tripeptide residue resulting from the combination of amino acids.

Lastly, the term heterocycle is understood to refer preferably to a piperidino, morpholino, pyrrolidino or piperazino radical optionally substituted in position 4 with a $C_1$–$C_6$ alkyl or a mono- or polyhydroxyalkyl radical as defined above.

When the radicals $R_4$ and $R_7$ represent a halogen atom, this is preferably a fluorine, bromine or chlorine atom.

Among the compounds of formula (I) above which fall within the scope of the present invention, mention may be made in particular of the following:

5-(3-tert-Butyl-4-methoxyphenyl)-2-thiopheneacrylic acid,
5-(3-tert-Butyl-4-methoxyphenyl)-2-thiophenepropiolic acid,
2-(3-tert-Butyl-4-methoxyphenyl)-4-thiopheneacrylic acid,
4-(3-tert-Butyl-4-methoxyphenyl)-2-thiopheneacrylic acid,
5-(3,5,5,8,8-Pentamethyl-5,6,7,8-tetrahydro-2-naphthyl)-2-thiopheneacrylic acid,
4-(3,5,5,8,8-Pentamethyl-5,6,7,8-tetrahydro-2-naphthyl)-2-thiopheneacrylic acid,
4-(5,6,7,8-Tetrahydro-5,5,8,8-tetramethyl-2-naphthyl)-2-thiopheneacrylic acid,
5-(3,5,5,9,8-Pentamethyl-5,6,7,8-tetrahydro-2-naphthyl)-2-thiophenepropiolic acid,
3-(3,5,5,8,8-Pentamethyl-5,6,7,8-tetrahydro-2-naphthyl)phenylpropiolic acid,
N-Methyl-4-(5,6,7,8-tetrahydro-5,5,8,8-tetramethyl-2-naphthyl)-2-pyrroleacrylic acid,
3-(5,6,7,8-Tetrahydro-5,5,8,8-tetramethyl-2-naphthyl)phenylacrylic acid,
N-Methyl-4-(3,5,5,8,8-pentamethyl-5,6,7,8-tetrahydro-2-naphthyl)-2-pyrroleacrylic acid,
4-(3,5,5,8,8-Pentamethyl-5,6,7,8-tetrahydro-2-naphthyl)-2-pyrroleacrylic acid,
3-(3,5,5,8,8-Pentamethyl-5,6,7,8-tetrahydro-2-naphthyl)phenylacrylic acid,
3-(5,6,7,8-Tetrahydro-5,5,8,8-tetramethyl-2-naphthyl)phenylpropiolic acid,
2-Methoxy-3-(3,5,5,8,8-pentamethyl-5,6,7,8-tetrahydro-2-naphthyl)phenylacrylic acid,
2-Propyloxy-3-(3,5,5,8,8-pentamethyl-5,6,7,8-tetrahydro-2-naphthyl)phenylacrylic acid,
2-Heptyloxy-3-(3,5,5,8,8-pentamethyl-5,6,7,8-tetrahydro-2-naphthyl)phenylacrylic acid,
2-Methoxymethoxy-3-(3,5,5,8,8-pentamethyl-5,6,7,8-tetrahydro-2-naphthyl)phenylacrylic acid,
2-Hydroxy-3-(3,5,5,8,8-pentamethyl-5,6,7,8-tetrahydro-2-naphthyl)phenylacrylic acid,
3-(3-Methoxy-5,6,7,8-tetrahydro-5,5,8,8-tetramethyl-2-naphthyl)phenylacrylic acid,
3-(3-Propyloxy-5,6,7,8-tetrahydro-5,5,8,8-tetramethyl-2-naphthyl)phenylacrylic acid,
3-(3-Heptyloxy-5,6,7,8-tetrahydro-5,5,8,8-tetramethyl-2-naphthyl)phenylacrylic acid,
3-(3-Methoxymethoxy-5,6,7,8-tetrahydro-5,5,8,8-tetramethyl-2-naphthyl)phenylacrylic acid,
3-(3-Hydroxy-5,6,7,8-tetrahydro-5,5,8,8-tetramethyl-2-naphthyl)phenylacrylic acid,
3-(4,4,7-Trimethylthiochroman-6-yl)phenylacrylic acid, N-Ethyl-3-(3,5,5,8,8-pentamethyl-5,6,7,8-tetrahydro-2-naphthyl)phenylacrylamide,
N-(4-Hydroxyphenyl)-3-(3,5,5,8,8-pentamethyl-5,6,7,8-tetrahydro-2-naphthyl)phenylacrylamide,
3-(3,5,5,8,8-Pentamethyl-5,6,7,8-tetrahydro-2-naphthyl)phenylacrylic acid morpholide,
Ethyl 3-(3,5,5,8,8-pentamethyl-5,6,7,8-tetrahydro-2-naphthyl)phenylacrylate,
3-[3-(3,5,5,8,8-Pentamethyl-5,6,7,8-tetrahydro-2-naphthyl)phenyl]but-2-enoic acid,
4-Methoxymethoxy-3-(3,5,5,8,8-pentamethyl-5,6,7,8-tetrahydro-2-naphthyl)phenylacrylic acid,
4-Hydroxy-3-(3,5,5,8,8-pentamethyl-5,6,7,8-tetrahydro-2-naphthyl)phenylacrylic acid,
4-Methoxy-3-(3,5,5,8,8-pentamethyl-5,6,7,8-tetrahydro-2-naphthyl)phenylacrylic acid,
4-Propyloxy-3-(3,5,5,8,8-pentamethyl-5,6,7,8-tetrahydro-2-naphthyl)phenylacrylic acid,
4-Heptyloxy-3-(3,5,5,8,8-pentamethyl-5,6,7,8-tetrahydro-2-naphthyl)phenylacrylic acid,
3-(3,5,5,8,8-Pentamethyl-5,6,7,8-tetrahydro-2-naphthyl)phenyl]acrolein,
3-[3-(3,5,5,8,8-Pentamethyl-5,6,7,8-tetrahydro-2-naphthyl)phenyl]prop-2-en-1-ol,
cis-3-[3-(3,5,5,8,8-Pentamethyl-5,6,7,8-tetrahydro-2-naphthyl)phenyl]but-2-enoic acid,
cis-3-(3,5,5,8,8-Pentamethyl-5,6,7,8-tetrahydro-2-naphthyl)phenylacrylic acid,
5-(3,5,5,8,8-Pentamethyl-5,6,7,8-tetrahydro-2-naphthyl)-3-pyridineacrylic acid,
3-(3-Butyl-5,6,7,8-tetrahydro-5,5,8,8-tetramethyl-2-naphthyl)phenylacrylic acid,
6-(3,5,5,8,8-Pentamethyl-5,6,7,8-tetrahydro-2-naphthyl)-2-pyridineacrylic acid.

According to the present invention, the compounds of formula (I) more particularly preferred are those for which at least one, and preferably all, of the following conditions are satisfied:

$R_1$ represents the radical —$COR_6$
Ar represents the radicals of formula (a) or (d)
X represents the radical

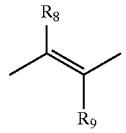

$R_2$ and $R_3$, taken together, form, with the adjacent aromatic ring, a 5- or 6-membered ring optionally substituted with methyl groups and/or optionally interrupted by an oxygen or sulphur atom.

The subject of the present invention is also processes for the preparation of the compounds of formula (I), in particular according to the reaction scheme given in FIG. 1.

Thus, the derivatives of formula (Ia) may be obtained (FIG. 1) from aldehyde or ketone derivatives (5) according to a Horner-type reaction with a lithium or sodium derivative of a phosphonate (7). The carbonyl compounds (5) may be obtained:

either by a coupling reaction between a boronic acid (3) and a halo derivative (4). This reaction is carried out in the presence of a palladium catalyst, for example tetrakis(triphenylphosphine)palladium according to the conditions described by N. Miyaura et al., Synthetic Communications (1981) 11(7), 513–519. The boronic acid derivative (3) may be obtained, for example, from the halo derivative (1) by conversion into the lithium reagent (2), followed by reaction with trimethyl borate and hydrolysis.

or by a coupling reaction between a zinc derivative (8) and a halogenated ester derivative (9) in the presence of a catalyst, for example a palladium or a nickel derivative ($NiCl_2$ dppe), followed by conversion of the ester function (10) into alcohol (11) and oxidation to aldehyde (5).

The compounds of formula (Ib) may be obtained (FIG. 1) from the acetylenic derivative (6) by reaction with n-butyllithium and then carboxylation in the presence of $CO_2$. The acetylenic compounds (6) may be obtained either:

from aldehyde derivatives (5) (when $R_8$ is a hydrogen atom), by reaction with carbon tetrabromide and triphenylphosphine in order to give a 2',2'-dibromostyrene derivative which is converted into acetylenic derivative by a non-nucleophilic base such as n-butyllithium, in an aprotic solvent such as tetrahydrofuran.

from ketone derivatives (5) (when $R_8$ is a lower alkyl) by a reaction sequence comprising treatment with a base such as lithium diisopropylamide and then with a dialkyl phosphate chloride and again with lithium diisopropylamide.

When $R_1$ represents the radical —COOH, the compounds are prepared by protecting $R_1$ with a protecting group of alkyl, allylic, benzylic or tert-butyl type.

The passage to the free form may be carried out:
in the case of an alkyl protecting group, using sodium hydroxide or lithium hydroxide in an alcoholic solvent such as methanol, or in THF.

in the case of an allylic protecting group, using a catalyst such as certain transition metal complexes in the presence of a secondary amine such as morpholine.

in the case of a benzylic protecting group, by debenzylation in the presence of hydrogen using a catalyst such as palladium-on-charcoal.

in the case of a protecting group of tert-butyl type, using trimethylsilyl iodide.

The subject of the present invention is also, as medicinal product, the compounds of formula (I) as defined above.

Some of these compounds are active in a test which consists in identifying molecules that are RXR agonists, as described in French patent application No. 95/07301 filed on 19 Jun. 1995 by the Applicant. This test comprises the following steps: (i) a sufficient amount of a compound which is an active ligand of at least one receptor of the steroidal/thyroidal receptor superfamily, other than a ligand which is specific for the RXR receptors, and which can heterodimerize with RXRa, such as an RAR-agonist molecule, is applied topically to part of the skin of a mammal, (ii) a molecule capable of exhibiting RXR-agonist activity is administered systemically or topically to this same part of the mammal's skin, before, during or after step (i), and (iii) the response on that part of the mammal's skin thus treated is evaluated. Thus, the response to a topical application, to a mammal's ear, of an RAR-agonist molecule, which corresponds to an increase in the thickness of this ear, may be increased by the systemic or topical administration of an RXR-agonist molecule. Some of the compounds according to the invention are also active in the test of differentiation of mouse embryonic teratocarcinoma cells (F9) (Cancer Research 43, pp. 5268, 1983) and/or in the test of inhibition of ornithine decarboxylase after induction with TPA in mice (Cancer Research 38, pp. 793–801, 1978). These tests show the activities of these compounds in the fields of cell differentiation and cell proliferation respectively.

The compounds according to the invention are particularly suitable in the following fields of treatment:

1) For treating dermatological complaints associated with a keratinization disorder which has a bearing on differentiation and on proliferation, in particular for treating common acne, comedones, polymorphonuclear leukocytes, rosacea, nodulocystic acne, acne conglobata, senile acne and secondary acnes such as solar, medication-related or profession-related acne.
2) For treating other types of keratinization disorder, in particular ichthyosis, ichthyosiform states, Darier's disease, palmoplantar keratoderma, leucoplasias and leucoplasiform states, and cutaneous or mucous (buccal) lichen.
3) For treating other dermatological complaints associated with a keratinization disorder with an inflammatory and/or immunoallergic component and, in particular, all forms of psoriasis, whether it is cutaneous, mucous or ungual psoriasis and even psoriatic rheumatism, or alternatively cutaneous atopy, such as eczema or respiratory atopy or alternatively gingival hypertrophy; the compounds may also be used for some inflammatory complaints which show no keratinization disorder,
4) For treating all dermal or epidermal hyperproliferations, whether benign or malignant and whether they are of viral origin or otherwise, such as common warts, flat warts and verruciform epidermodysplasia, it being possible for the oral or florid papillomatoses and the hyperproliferations to be induced by ultraviolet radiation, in particular in the case of basocellular and spinocellular epitheliona,
5) For treating other dermatological disorders such an bullosis and collagen diseases,
6) For treating certain ophthalmological disorders, in particular corneopathies,
7) For repairing or combating ageing of the skin, whether this is light-induced or chronological ageing, or for reducing actinic keratoses and pigmentations, or any pathologies associated with chronological or actinic ageing,
8) For preventing or curing the stigsata of epidermal and/or dermal atrophy induced by local or systemic corticosteroids, or any other form of cutaneous atrophy,
9) For preventing or treating cicatrization disorders or for preventing or repairing vibices,
10) For combating disorders of sebaceous functioning such as the hyperseborrhoea of acne or simple seborrhoea,
11) In the treatment or prevention of cancerous or precancerous states,
12) In the treatment of inflammatory complaints such as arthritis,
13) In the treatment of any general or skin complaint of viral origin,
14) In the prevention or treatment of alopecia,
15) In the treatment of dermatological or general complaints having an immunological component,
16) In the treatment of complaints of the cardiovascular system such as arteriosclerosis or hypertension, as well as insulin-independent diabetes,
17) In the treatment of skin disorders caused by exposure to UV radiation.

In the therapeutic fields mentioned above, the compounds according to the invention may advantageously be employed in combination with other compounds having retinoid-type activity, with D vitamins or derivatives thereof, with corticosteroids, with anti-free-radical agents, α-hydroxy or α-keto acids or derivatives thereof, or alternatively with ion-channel blockers. The expression D vitamins or derivatives thereof is understood to refer, for example, to vitamin $D_2$ or $D_3$ derivatives and in particular 1,25-dihydroxy vitamin $D_3$. The expression anti-free-radical agent is understood to refer, for example, to α-tocopherol, superoxide dismutase, ubiquinol or certain metal-chelating agents. The expression α-hydroxy or α-keto acids or derivatives thereof is understood to refer, for example, to lactic acid, malic acid, citric acid, glycolic acid, mandelic acid, tartaric acid, glyceric acid or ascorbic acid or salts, amides or esters thereof. Lastly, the expression ion-channel blockers is understood to refer, for example, to Minoxidil (2,4-diamino-6-piperidinopyrimidine 3-oxide) and derivatives thereof.

The subject of the present invention is also medicinal compositions containing at least one compound of formula (I) as defined above, one of the optical or geometric isomers thereof or one of the salts thereof.

The subject of the present invention is thus a novel medicinal composition intended in particular for treating the abovementioned complaints, and which is characterized in that it comprises, in a pharmaceutically acceptable support which is compatible with the mode of administration-selected for this composition, at least one compound of formula (I), one of the optical or geometric isomers thereof or one of the salts thereof.

The compounds according to the invention may be administered enterally, parenterally, topically or ocularly.

Via the enteral route, the medicinal products may be in the form of tablets, gelatin capsules, sugar-coated tablets, syrups, suspensions, solutions, powders, granules, emulsions, microspheres or nanospheres or polymeric or lipidvesicles which allow controlled release. Via the parenteral route, the compositions may be in the form of solutions or suspensions for infusion or for injection.

The compounds according to the invention are generally administered at a daily dose of about 0.01 mg/kg to 100 mg/kg of body weight, taken in 1 to 3 doses.

Via the topical route, the pharmaceutical compositions based on compounds according to the invention are more particularly intended for treating the skin and mucous membranes and may, in this case, be in the form of ointments, creams, milks, salves, powders, impregnated pads, solutions, gels, sprays, lotions or suspensions. They may also be in the form of microspheres or nanospheres or polymeric or lipid vesicles or polymeric patches and hydrogels which allow controlled release. These topical-route compositions may moreover be either in anhydrous form or in an aqueous form, depending on the clinical indication.

Via the ocular route, they are mainly eyedrops.

The compositions for topical or ocular use contain at least one compound of formula (I) defined above, or one of the optical or geoetric isomers thereof, or alternatively one of the salts thereof, at a concentration preferably of between 0.001% and 5% by weight relative to the total weight of the composition.

The compounds of formula (I) according to the invention also find an application in the cosmetic field, in particular in body and hair hygiene and especially for treating skin-types with a tendency towards acne, for promoting the regrowth of the hair, for combating hair loss, for controlling the greasy appearance of the skin or the hair, in protection against the harmful effects of sunlight or in the treatment of physiologically dry skin-types, and for preventing and/or combating light-induced or chronological ageing.

In the cosmetic field, the compounds according to the invention may also advantageously be employed in combination with other compounds having retinoid-type activity, with D vitamins or derivatives thereof, with corticosteroids, with anti-free-radical agents, α-hydroxy or α-keto acids or derivatives thereof, or alternatively with ion-channel blockers, all of these different products being as defined above.

The present invention is this also directed towards a cosmetic composition which is characterized in that it comprises, in a cosmetically acceptable support which is suitable for topical application, at least one compound of formula (I) as defined above, or one of the optical or geometric isomers thereof or one of the salts thereof, it being possible in particular for this cosmetic composition to be in the form of a cream, a milk, a lotion, a gel, microspheres or nanospheres or polymeric or lipid vesicles, a soap or a shampoo.

The concentration of compound of formula (I) in the cosmetic compositions according to the invention is advantageously between 0.001% and 3% by weight relative to the composition as a whole.

The medicinal and cosmetic compositions according to the invention may also contain inert additives or even pharmacodynmically or cosmetically active additives or combinations of these additives and, in particular, wetting agents; depigmenting agents such as hydroquinone, azelaic acid, caffeic acid or kojic acid; emollients; moisturizing agents such as glycerol, PEG 400, thiamorpholinone and derivatives thereof, or urea; anti-seborrhoea or anti-acne agents such as S-carboxymethylcysteine, S-benzylcysteamine, the salts and the derivatives thereof, or benzoyl peroxide; antibiotics such as erythromycin and esters thereof, neomycin, clindamycin and esters thereof, and tetracyclines; antifungal agents such as ketoconazole or 4,5-polymethylene-3-isothiazolidones; agents for promoting the regrowth of the hair, such as minoxidil (2,4-diamino-5-piperidinopyridine 3-oxide) and derivatives thereof, diazoxide (7-chloro-3-methyl-1,2,4-benzothiadiazine 1,1-dioxide) and phenytoin (5,4-diphenylimidazolidine-2,4-dione); non-steroidal anti-inflammatory agents; carotenoids and, in particular, b-carotene; anti-psoriatic agents such as anthraline and derivatives thereof and, lastly, eicosa-5,8,11,14-tetraynoic acid and eicosa-5,8,11-triynoic acid, the esters and the amides thereof.

The compositions according to the invention may also contain flavour-enhancing agents, preserving agents such as para-hydroxybenzoic acid esters, stabilizing agents, moisture regulators, pH regulators, osmotic pressure modifiers, emulsifying agents, UV-A and UV-B screening agents, and antioxidants such as α-tocopharol, butylhydroxyanisole or butylhydroxytoluene.

Several examples of the production of active compounds of formula (I) according to the invention, as well as various solid formulations based on such compounds, will now be given by way of illustration and with no limitation. In the preceding description and the following examples, percentages are given by weight unless otherwise stated.

EXAMPLE 1

5-(3-tert-Butyl-4-methoxyphenyl)-2-thiopheneacrylic acid (a) Methyl 5-(3-tert-butyl-4-methoxyphenyl)-2-thiophenecarboxylate A solution of 2 g (8.2 mmol) of 3-tert-butyl-4-methoxybromobenzene is added dropwise to a suspension of 300 mg (12 mmol) of magnesium in 10 ml of THF. Once the addition is complete, the mixture is refluxed for one hour. At room temperature, 1.35 g (9.9 mmol) of anhydrous zinc chloride are added and the mixture is stirred for one hour. 1.2 g (5.5 mmol) of methyl 5-bromo-2-thiophenecarboxylate and 60 mg (0.12 mmol) of the $NiCl_2$/DPPE complex are then added successively and the mixture is left stirring at room temperature for 12 hours. The reaction medium is poured into ice-water and extracted with ethyl ether and the organic phase is separated out after settling has taken place, dried over magnesium sulphate and evaporated. The residue obtained is chromatographed on a column of silica eluted with a mixture of hexane and dichloromethane (50/50% by volume). After evaporation of the solvents, 1.56 g (93%) of the expected methyl ester are collected, with a melting point of 94–5° C.

(b) 5-(3-tert-Butyl-4-methoxyphenyl)-2-thiophenemethanol 1.5 g (5 mmol) of the above methyl ester and 50 ml of anhydrous THF are introduced into a three-necked flask under a stream of nitrogen. 280 mg (7.4 mmol) of lithium aluminium hydride are added and the mixture is refluxed for four hours. It is hydrolyzed with potassium sodium tartrate solution, the salt is filtered off and the filtrate is evaporated. The residue obtained is purified by chromatography on a column of silica eluted with a mixture of dichloromethane and hexane (70/30% by volume). After evaporation of the solvents, 1.26 g (92%) of the expected alcohol are recovered, in the form of a colourless oil.

(c) 5-(3-tert-Butyl-4-methoxyphenyl)-2-thiophenecarboxaldehyde 7.15 g (19 mmol) of pyridinium dichromate and 350 ml of dichloromethane are introduced into a round-bottomed flask. A solution of 3.9 g (14 mmol) of 5-(3-tert-butyl-4-methoxyphenyl)-2-thiophenemethanol in 50 ml of dichloromethane is added dropwise, at 0° C., and the mixture is stirred at room temperature for two hours. The reaction medium is filtered through silica and, after evaporation, 3.26 g (84%) of the expected aldehyde are recovered, in the form of a brown oil.

(d) Ethyl 5-(3-tert-butyl-4-methoxyphenyl)-2-thiopheneacrylate 200 mg (6.6 mmol) of sodium hydride (80% in oil) and 50 ml of dimethoxyethane are introduced into a three-necked flask under a stream of nitrogen and a solution of 1.3 ml (6.6 mmol) of triethyl phosphoacetate in 10 ml of dimethoxyethane is added dropwise. The mixture is stirred at room temperature for one hour and then, at 0° C., a solution of 1.5 g (5.5 mmol) of 5-(3-tert-butyl-4-methoxyphenyl)-2-thiophenecarboxaldehyde in 20 ml of dimethoxyethane is added dropwise. The reaction medium is stirred at room temperature for four hours and is then poured into water and extracted with ethyl ether, and the organic phase is separated out after settling has taken place, dried over magnesium sulphate and evaporated. The residue obtained is purified by chromatography on a column of silica eluted with a mixture of dichloromethane and hexane (30/70% by volume); 1.88 g (100%) of the expected ethyl easter are collected, in the form of a brown oil.

(e) 5-(3-tert-Butyl-4-methoxyphenyl)-2-thiopheneacrylic acid 1.88 g (5.4 mmol) of the above ethyl ester, 20 ml of methanol and 1.88 g (47 mmol) of sodium hydroxide ae introduced into a round-bottomed flask and the mixture is refluxed for four hours. The reaction medium is evaporated to dryness, the residue is taken up in water and acidified to pH 1, and the solid is filtered off and dried. The solid obtained is recrystallized from ethanol, filtered off and dried. 1.09 g (63%) of 5-(3-tert-butyl-4-methoxyphenyl)-2-thiopheneacrylic acid are collected, with a melting point of 218–9° C.

EXAMPLE 2

5-(3-tert-Butyl-4-methoxyphenyl)-2-thiophenepropiolic acid (a) 2',2'-Dibromo-5-(3-tert-butyl-4-methoxyphenyl)-2-thiopheneethylene 1.79 g (6.5 mmol) of 5-(3-tert-butyl-4-methoxyphenyl)-2-thiophenecarboxaldehyde prepared in Example 1 (c) and 50 ml of dichloromethane are introduced into a round-bottomed flask. 4.32 g (13 mmol) of carbon tetrabromide, 3.41 g (13 mmol) of triphenylphosphine and 850 mg (13 mmol) of zinc powder are successively added and the mixture is stirred at room temperature for two hours. The reaction medium is evaporated and the residue obtained is purified by chromatography on a column of silica eluted with dichloromethane. 2.5 g (89%) of the expected product are collected.

(b) 5-(3-tert-Butyl-4-methoxyphenyl)-2-thiopheneacetylene 2.48 g (5.7 mmol) of 2',2'-dibromo-5-(3-tert-butyl-4-methoxyphenyl)-2-thiopheneethylene and 40 ml of THF are introduced into a three-necked flask under a stream of nitrogen. 5.1 ml (12.7 mmol) of n-butyllithium solution (2.5 M in hexane) are added dropwise, at −78° C., and the mixture is allowed to return to room temperature over one hour. The reaction medium is poured into water and extracted with ethyl ether, and the organic phase is separated out after settling has taken place, dried over magnesium sulphate and evaporated. The residue obtained is purified by chromatography on a column of silica eluted with heptane. 1.1 g (71%) of the expected acetylenic derivative are collected, in the form of a yellow oil.

(c) 5-(3-tert-Butyl-4-methoxyphenyl)-2-thiophenepropiolic acid 1.1 g (4 mmol) of the above acetylenic derivative and 20 ml of THF are introduced into a three-necked flask under a stream of nitrogen. 1.95 ml (4.9 mmol) of n-butyllithium (2.5 M in hexane) are added dropwise, at −78° C., and the mixture in stirred for thirty minutes. A stream of $CO_2$ is passed through at −78° C. for fifteen minutes and the mixture is allowed to return to room temperature. The reaction medium is poured into aqueous ammonium chloride solution and extracted with ethyl ether, and the organic phase is separated out after settling has taken place, dried over magnesium sulphate and evaporated. The residue obtained in purified by chromatography on a column of silica eluted with dichloromethane. After evaporation of the solvents, 300 mg (23%) of 5-(3-tert-butyl-4-methoxyphenyl)-2-thiophenepropiolic acid are collected, with a melting point of 124–6° C.

EXAMPLE 3

2-(3-tert-Butyl-4-methoxyphenyl)-4-thiopheneacrylic acid (a) 3-tert-Butyl-4-methoxyphenylboronic acid 4 g (16.5 mmol) of 3-tert-butyl-4-methoxybromobenzene and 50 ml of THF are introduced into a three-necked flask under a stream of nitrogen. 7.9 ml (19.8 mmol) of n-butyllithium (2.5 M in hexane) are added dropwise at −78° C., the mixture is stirred for 15 minutes at this temperature, 5.6 ml (49.5 mmol) of trimethyl borate are added and the mixture is stirred for 2 hours. 20 ml of hydrochloric acid (1 N) are added at −50° C. and the mixture is allowed to return to room temperature. The reaction medium is extracted with ethyl ether and the organic phase is separated out after settling has taken place, dried over magnesium sulphate and evaporated. 3.79 g (100%) of the expected boronic acid are collected, which is used in its present state for the rest of the synthesis.

(b) Ethyl 2-(3-tert-butyl-4-methoxyphenyl)-4-thiophenecarboxylate 260 mg (0.5 mmol) of tetrakis(triphenylphosphine) palladium(0), 50 ml of toluene and 2.59 g (10.9 mmol) of ethyl 2-bromo-4-thiophenecarboxylate are introduced into a three-necked flask under a stream of nitrogen and the mixture is stirred at room temperature for 20 minutes. 3.7 g (16.5 mmol) of 3-tert-butyl-4-methoxyphenylboronic acid and 11 ml of aqueous sodium carbonate solution (2 N) are then added and the mixture is refluxed for 8 hours. The reaction medium is evaporated to dryness, the residue is taken up in water and ethyl ether and the organic phase is separated out after settling has taken place, dried over magnesium sulphate and evaporated. The residue is purified by chromatography on a column of silica eluted with a mixture of ethyl acetate and heptane (10/90% by volume). 3.53 g (69%) of ethyl 2-(3-tert-butyl-4-methoxyphenyl)-4-thiophenecarboxylate are obtained.

(c) 2-(3-tert-Butyl-4-methoxyphenyl)-4-thiophenemethanol

In a similar manner to Example 1(b), starting with 3.5 g (11 mmol) of ethyl 2-(3-tert-butyl-4-methoxyphenyl)-4-thiophenecarboxylate, 3.2 g (100%) of the expected alcohol are obtained in the form of a brown oil.

(d) 2-(3-tert-Butyl-4-methoxyphenyl)-4-thiophenecarboxaldehyde

In a similar manner to Example 1(c), starting with 3.2 g (11 mmol) of the above alcohol, 2.3 g (76%) of 2-(3-tert-butyl-4-methoxyphenyl)-4-thiophenecarboxaldehyde are obtained in the form of a brown oil.

(e) Ethyl 2-(3-tert-butyl-4-methoxyphenyl)-4-thiopheneacrylate

In a similar manner to Example 1(d), by reaction of 1.3 g (4.7 mmol) of 2-(3-tert-butyl-4-methoxyphenyl)-4-thiophenecarboxaldehyde with 1.28 g (5.7 mmol) of triethyl phosphonoacetate, 1.1 g (67%) of the expected ethyl eater are obtained, with a melting point of 119–20° C.

(f) 2-(3-tert-Butyl-4-methoxyphenyl)-4-thiopheneacrylic acid

In a similar manner to Example 1(e), starting with 1.1 g (3.2 mmol) of the above ethyl ester, 750 mg (74%) of 2-(3-tert-butyl-4-methoxyphenyl)-4-thiopheneacrylic acid are obtained, with a melting point of 197–8° C.

EXAMPLE 4

4-(3-tert-Butyl-4-methoxyphenyl)-2-thiopheneacrylic acid (a) 4-(3-tert-Butyl-4-methoxyphenyl)-2-thiophenecarboxaldehyde In a similar manner to Example 3(b), by reaction of 2.68 g (12.3 mmol) of 3-tert-butyl-4-methoxyphenylboronic acid with 1.55 g (2.12 mmol) of 4-bromo-2-thiophenecarboxaldehyde, 2.13 g (95%) of 4-(3-tert-butyl-4-methoxyphenyl)-2-thiophenecarboxaldehyde are obtained in the form of a yellow oil.

(b) Ethyl 4-(3-tert-butyl-4-methoxyphenyl)-2-thiopheneacrylate

In a similar manner to Example 1(d), by reaction of 1.2 g (4.3 mmol) of 4-(3-tert-butyl-4-methoxyphenyl)-2-thiophenecarboxaldehyde with 1.17 g (5.2 mmol) of triethyl phosphonoacetate, 1.55 g (100%) of the expected ethyl ester are obtained in the form of an oil.

(c) 4-(3-tert-Butyl-4-methoxyphenyl)-2-thiopheneacrylic acid

In a similar manner to Example 1(e), starting with 1.55 g (4.5 mmol) of the above ethyl ester, 1.14 g (88%) of 4-(3-tert-butyl-4-methoxyphenyl)-2-thiopheneacrylic acid are obtained, with a melting point of 206–7° C.

EXAMPLE 5

5-(3,5,5,5,8-Pentamethyl-5,6,7,8-tetrahydro-2-naphthyl)-2-thiopheneacrylic acid (a) 3,5,5,8,8-Pentamethyl-5,6,7,8-tetrahydro-2-naphthylboronic acid In a similar manner to Example 3 (a), starting with 5 g (17.8 mmol) of 3,5,5,8,8-pentamethyl-5,6,7,6-tetrahydro-2-bromonaphthalene, 4.22 g (100%) of boronic acid are obtained.

(b) 5-(3,5,5,8,8-Pentamethyl-5,6,7,8-tetrahydro-2-naphthyl)-2-thiophenecarboxaldehyde In a similar manner to Example 3(b), by reaction of 4.2 g (17 mmol) of 3,5,5,8,8-pentamethyl-5,6,7,8-tetrahydro-2-naphthylboronic acid with 2.17 g (11.3 mmol) of 5-bromo-2-thiophenecarboxaldehyde, 2.1 g (60%) of the expected aldehyde are obtained, with a melting point of 130–5° C.

(c) Ethyl 5-(3,5,5,8,8-pentamethyl-5,6,7,8-tetrahydro-2-naphthyl)-2-thiopheneacrylate In a similar manner to Example 1(d), by reaction of 2 g (6.4 mmol) of 5-(3,5,5,8,8-pentamethyl-5,6,7,8-tetrahydro-2-naphthyl)-2-thiophenecarboxaldehyde with 1.73 g (7.7 mmol) of triethyl phosphonoacetate, 2.02 g (82%) of the expected ethyl ester are obtained.

(e) 5-(3,5,5,8,8-Pentamethyl-5,6,7,8-tetrahydro-2-naphthyl)-2-thiopheneacrylic acid In a similar manner to Example 1(e), starting with 2 g (5.2 mmol) of the above ethyl ester, 1.79 g (96%) of 5-(3,5,5,8, 8-pentamethyl-5,6,7,8-tetrahydro-2-naphthyl)-2-thiopheneacrylic acid are obtained, with a melting point of 175–7° C.

EXAMPLE 6

4-(3,5,5,8,8-Pentamethyl-5,6,7,8-tetrahydro-2-naphthyl)-2-thiopheneacrylic acid (a) 4-(3,5,5,5,8,8-Pentamethyl-5,6,7,8-tetrahydro-2-naphthyl)-2-thiophenecarboxaldehyde In a similar manner to Example 3(b), by reaction of 4.2 g (17 mmol) of 3,5,5,8,8-pentamethyl-5,6,7,8-tetrahydro-2-naphthylboronic acid with 2.17 g (11.3 mmol) of 4-bromo-2-thiophenecarboxaldehyde, 2.75 g (78%) of the expected aldehyde are obtained, with a melting point of 144–6° C.

(b) Ethyl 4-(3,5,5,8,8-pentamethyl-5,6,7,8-tetrahydro-2-naphthyl)-2-thiopheneacrylate In a similar manner to Example 1(d), by reaction of 2.7 g (8.6 mmol) of 4-(3,5,5,8,8-pentamethyl-5,6,7,8-tetrahydro-2-naphthyl)-2-thiophenecarboxaldehyde with 2.1 ml (10.4 mmol) of triethyl phosphonoacetate, 2.76 g (84%) of the expected ethyl ester are obtained.

(c) 4-(3,5,5,8,8-Pentamethyl-5,6,7,8-tetrahydro-2-naphthyl)-2-thiopheneacrylic acid In a similar manner to Example 1(e), starting with 2.7 g (7.1 mmol) of the above ethyl ester, 2.5 g (98%) of 4-(3,5, 5,8,8-pentamethyl-5,6,7,8-tetrahydro-2-naphthyl)-2-thiopheneacrylic acid are obtained, with a melting point of 215–20° C.

EXAMPLE 7

4-(5,6,7,8-Tetrahydro-5,5,8,8-tetramethyl-2-naphthyl)-2-thiopheneacrylic acid (a) 5,6,7,8-Tetrahydro-5,5,8,8-tetramethyl-2-naphthylboronic acid In a similar manner to Example 3(a), starting with 5 g (18.7 mmol) of 5,6,7,8-tetrahydro-5,5,8,8-tetramethyl-2-bromonaphthalene, 4.3 g (100%) of the expected boronic acid are obtained.

(b) 4-(5,6,7,8-Tetrahydro-5,5,9,8-tetramethyl-2-naphthyl)-2-thiophenecarboxaldehyde In a similar manner to Example 3(b), by reaction of 4.3 g (18.7mmol) of 5,6,7,8-tetrahydro-5,5,8,6-tetramethyl-2-naphthylboronic acid with 2.36 g (12.3 mmol) of 4-bromo-2-thiophenecarboxaldehyde, 2.3 g (63%) of the expected aldehyde derivative are obtained, with a melting point of 84–5° C.

c) Ethyl 4-(5,6,7,8-tetrahydro-5,5,8,8-tetramethyl-2-naphthyl)-2-thiopheneacrylate In a similar manner to Example 1(d), by reaction of 2.28 g (8.3 mmol) of (5,6,7,8-tetrahydro-5,5,8,8-tetramethyl-2-naphthyl)-2-thiophenecarboxaldehyde with 2 ml (9.9 mmol) of triethyl phosphonoacetate, 810 mg (26%) of the expected ethyl ester are obtained, with a melting point of 82–4° C.

(d) 4-(5,6,7,8-Tetrahydro-5,5,8,8-tetramethyl-2-naphthyl)-2-thiopheneacrylic acid In a similar manner to Example 1(e), starting with 810 mg (2.2 mmol) of the above ethyl ester, 720 mg (96%) of 4-(5,6,7,8-tetrahydro-5,5,8,8-tetramethyl-2-naphthyl)-2-thiopheneacrylic acid are obtained, with a melting point of 182–5° C.

EXAMPLE 8

5-(3,5,5,8,8-Pentamethyl-5,6,7,8-tetrahydro-2-naphthyl)-2-thiophenepropiolic acid (a) 2',2'-Dibromo-5-(3,5,5,8,8-pentamethyl-5,6,7,8-tetrahydro-2-naphthyl)-2-thiopheneethylene In a similar manner to Example 2(a), starting with 3 g (9.6 mmol) of 5-(3,5,5,8,8-pentamethyl-5,6,7,8-tetrahydro-2-naphthyl)-2-thiophenecarboxaldehyde, 4.56 g (100%) of 2',2'-dibromo-5-(3,5,5,8,8-pentamethyl-5,6,7,8-tetrahydro-2-naphthyl)-2-thiopheneethylene are obtained.

(b) 5-(3,5,5,8,8-Pentamethyl-5,6,7,6-tetrahydro-2-naphthyl)-2-thiopheneacetylene In a similar manner to Example 2(b), starting with 4.5 g (9.6 mmol) 2',2'-dibromo-5-(3,5,5,8,8-pentamethyl-5,6,7,8-tetrahydro-2-naphthyl)-2-thiopheneethylene, 1.42 g (48%) of 5-(3,5,5,8,8-pentamethyl-5,6,7,8-tetrahydro-2-naphthyl)-2-thiopheneacetylene are obtained.

(c) 5-(3,5,5,8,8-Pentamethyl-5,6,7,8-tetrahydro-2-naphthyl)-2-thiophenepropiolic acid In a similar manner to Example 2(c), starting with 1.4 g (4.5 mmol) of the above acetylenic derivative, 800 mg (51%) of 5-(3,5,5,8,8-pentamethyl-5,6,7,8-tetrahydro-2-naphthyl)-2-thiophenepropiolic acid are obtained, with a melting point of 138–40° C.

EXAMPLE 9

3-(3,5,5,8,8-Pentamethyl-5,6,7,8-tetrahydro-2-naphthyl) phenylpropiolic acid (a) 3,5,5,8,8-Pentamethyl-5,6,7,8-tetrahydro-2-naphthylboronic acid 100 g (0.356 mol) of 2-bromo-3,5,5,8,8-pentamethyl-5,6, 7,8-tetrahydro-2-naphthalene and 1 litre of THF are introduced into a two-litre reactor under a stream of nitrogen, and the solution is cooled to −60° C. 157 ml (0.392 mol) of n-butyllithium (2.5 M in hexane) are added dropwise and the mixture in stirred for one hour. 121 ml (1.07 mol) of trimethyl borate are added dropwise at −70° C. and the mixture is stirred for one hour. 500 ml of hydrochloric acid (1 N) are added at −35° C. and the mixture is allowed to return to room temperature. The reaction medium is extracted with ethyl acetate and the organic phase in separated out after settling has taken place, washed twice with 500 ml of hydrochloric acid (1 N), dried over magnesium sulphate and evaporated. 83 g (95%) of the expected boronic acid are collected.

(b) 3-(3,5,5,8,8-Pentamethyl-5,6,7,8-tetrahydro-2-naphthyl) benzaldehyde 700 ml of DME, 2.4 g (2 mmol) of tetrakistriphenylphosphinepalladium(0) and 8.44 g (45.6 mmol) of 3-bromobenzaldehyde are introduced into a three-necked flask under a stream of nitrogen and the mixture is stirred for 10 minutes. A solution of 17 g (69.1 mmol) of 3,5,5,8,8-pentamethyl-5,6,7,8-tetrahydro-2-naphthylboronic acid in 25 ml of ethanol are then added, followed by 46 ml (91 mmol) of potassium carbonate solution (2 M) and the mixture is refluxed for four hours. The reaction medium is cooled and filtered and the solid is washed with bicarbonate solution and then with ethyl acetate. The solid obtained is recrystallized from ethanol and 7 g (50%) of the expected aldehyde are collected, with a melting point of 104–5° C.

(c) 2',2'-Dibromo-3-(3,5,5,8,8-pentamethyl-5,6,7,8-tetrahydro-2-naphthyl)phenylethylene In a similar manner to Example 2(a), starting with 2 g (6.5 mmol) of the above aldehyde, 1.96 g (65%) of the expected product are obtained in the form of a colourless oil.

(d) 3-(3,5,5,8,8-Pentamethyl-5,6,7,8-tetrahydro-2-naphthyl)phenylacetylene

In a similar manner to Example 2(b), starting with 1.96 g (4.23 mmol) of 2',2'-dibromo-3-(3,5,5,8,8-pentamethyl-5,6,7,8-tetrahydro-2-naphthyl)phenylethylene, 1.29 g (99%) of the expected acetylenic derivative are obtained in the form of a pale yellow oil.

(e) 3-(3,5,5,8,8-Pentamethyl-5,6,7,8-tetrahydro-2-naphthyl)phenylpropiolic acid

In a similar manner to Example 2(c), starting with 1.17 g (3.9 mmol) of the above acetylenic derivative, 900 mg (67%) of 3-(3,5,5,8,8-pentamethyl-5,6,7,8-tetrahydro-2-naphthyl)phenylpropiolic acid are obtained, with a melting point of 180–1° C.

EXAMPLE 10

N-Methyl-4-(5,6,7,8-tetrahydro-5,5,8,8-tetramethyl-2-naphthyl)-2-pyrroleacrylic acid (a) 4-(5,6,7,8-Tetrahydro-5,5,8,8-tetramethyl-2-naphthyl)-2-pyrrolecarboxaldehyde In a similar manner to Example 3(b), by reaction of 5.9 g (25.6 mmol) of 5,6,7,8-tetrahydro-5,5,8,8-tetramethyl-2-naphthylboronic acid with 3.7 g (21.3 mmol) of 4-bromo-2-pyrrolecarboxaldehyde, 1.3 g (21.6%) of the expected product are obtained, with a melting point of 211–2° C.

(b) N-Methyl-4-(5,6,7,8-tetrahydro-5,5,8,8-tetramethyl-2-naphthyl)-2-pyrrolecarboxaldehyde 1.3 g (4.6 mmol) of 4-(5,6,7,8-tetrahydro-5,5,8,8-tetramethyl-2-naphthyl)-2-pyrrolecarboxaldehyde and 50 ml of THF are introduced into a three-necked flask under a stream of nitrogen. 300 mg (10 mmol) of sodium hydride (80% in oil) are added portionwise and the mixture is stirred until the evolution of gas has ceased. 640 µl (10 mmol) of iodomethane are then added and the mixture is stirred at room temperature for one hour. The reaction medium is poured into water and extracted with ethyl acetate, and the organic phase is separated out after settling has taken place, dried over magnesium sulphate and evaporated. The residue obtained is purified by chromatography on a column of silica eluted with a mixture of dichloromethane and heptane (70/30). After evaporation of the solvents, 600 mg (44%) of the expected product are collected.

(c) Ethyl N-methyl-4-(5,6,7,8-tetrahydro-5,5,8,8-tetramethyl-2-naphthyl)-2-pyrroleacrylate In a similar manner to Example 1(d), by reaction of 480 mg (1.3 mmol) of N-methyl-4-(5,6,7,8-tetrahydro-5,5,8,8-tetramethyl-2-naphthyl)-2-pyrrolecarboxaldehyde with 400 µl (152 mmol) of triethyl phosphonoacetate, 350 mg of the expected ethyl ester are obtained in the form of an oil.

(d) N-Methyl-4-(5,6,7,8-tetrahydro-5,5,8,8-tetramethyl-2-naphthyl)-2-pyrroleacrylic acid In a similar manner to Example 1(e), starting with 350 mg (0.94mmol) of the above ethyl ester, 170 mg (23%) of N-methyl-4-(5,6,7,8-tetrahydro-5,5,8,8-tetramethyl-2-naphthyl)-2-pyrroleacrylic acid are obtained, with a melting point of 165–6° C.

EXAMPLE 11

3-(5,6,7,8-Tetrahydro-5,5,8,8-tetramethyl-2-naphthyl)phenylacrylic acid (a) 3-(5,6,7,8-Tetrahydro-5,5,8,8-tetramethyl-2-naphthyl)phenylcarboxaldehyde In a similar manner to Example 3(b), by reaction of 6.43 g (27.7 mmol) of 5,6,7,8-tetrahydro-5,5,8,8-tetramethyl-2-naphthylboronic acid with 2.7 ml (23.1 mmol) of 4-bromobenzaldehyde, 2.05 g (24%) of 3-(5,6,7,8-tetrahydro-5,5,8,8-tetramethyl-2-naphthyl)phenylcarboxaldehyde are obtained in the form of a pale yellow oil.

b) Ethyl 3-(5,6,7,8-tetrahydro-5,5,8,8-tetramethyl-2-naphthyl)phenylacrylate

In a similar manner to Example 1(d), by reaction of 800 mg (2.7 mmol) of 3-(5,6,7,8-tetrahydro-5,5,8,8-tetramethyl-2-naphthyl)phenylcarboxaldehyde with 650 ml (3.3 mmol) of triethyl phosphonoacetate, 900 mg (91%) of the expected ethyl ester are obtained in the form of a colourless oil.

(c) 3-(5,6,7,8-Tetrahydro-5,5,8,8-tetramethyl-2-naphthyl)phenylacrylic acid

In a similar manner to Example 1(e), starting with 1.22 g (2.7 mmol) of the above ethyl ester, 380 mg (41%) of 3-(5,6,7,8-tetrahydro-5,5,8,8-tetramethyl-2-naphthyl)phenylacrylic acid are obtained, with a melting point of 210–1° C.

EXAMPLE 12

N-Methyl-4-(3,5,5,8,8-pentamethyl-5,6,7,8-tetrahydro-2-naphthyl)-2-pyrroleacrylic acid (a) N-Methyl-4-bromo-2-pyrrolecarboxaldehyde In a similar manner to Example 10(b), by reaction of 4 g (23 mmol) of 4-bromo-2-pyrrolecarboxaldehyde with 1.7 ml (27.6 ml) of iodomethane, 2.3 g (50%) of the expected product are obtained, with a melting point of 123–4° C.

(b) N-Methyl-4-(3,5,5,8,8-pentamethyl-5,6,7,8-tetrahydro-2-naphthyl)-2-pyrrolecarboxaldehyde In a similar manner to Example 3(b), by reaction of 3 g (12.1 mmol) of 3,5,5,8,8-pentamethyl-5,6,7,8-tetrahydro-2-naphthylboronic acid with 1.9 g (10.1 mmol) of N-methyl-4-bromo-2-pyrrolecarboxaldehyde, 1.85 g (59%) of the expected product are obtained in the form of a pale yellow oil.

(c) Ethyl N-methyl-4-(3,5,5,8,8-pentamethyl-5,6,7,8-tetrahydro-2-naphthyl)-2-pyrroleacrylate In a similar tanner to Example 1(d), by reaction of 1.85 g (6 mmol) of N-methyl-4-(3,5,5,8,8-pentamethyl-5,6,7,8-tetrahydro-2-naphthyl)-2-pyrrolecarboxaldehyde with 1.4 ml (7.2 mmol) of triethyl phosphonoacetate, 2.1 g (92%) of the expected ethyl ester are obtained in the form of an orange-coloured oil.

(d) N-Methyl-4-(3,5,5,8,8-pentamethyl-5,6,7,8-tetrahydro-2-naphthyl)-2-pyrroleacrylic acid In a similar manner to Example 1(e), starting with 2 g (5.3 mmol) of the above ethyl ester, 730 mg (39.5%) of N-methyl-4-(3,5,5,8,8-pentamethyl-5,6,7,8-tetrahydro-2-naphthyl)-2-pyrroleacrylic acid are obtained, with a melting point of 185–6° C.

EXAMPLE 13

4-(3,5,5,8,8-Pentamethyl-5,6,7,8-tetrahydro-2-naphthyl)-2-pyrroleacrylic acid (a) 4-(3,5,5,8,8-Pentamethyl-5,6,7,8-tetrahydro-2-naphthyl)-2-pyrrolecarboxaldehyde In a similar manner to Example 3(b), by reaction of 2.47 g (10 mmol) of 3,5,5,8,8-pentamethyl-5,6,7,9-tetrahydro-2-naphthylboronic acid with 1.5 g (8.4 mmol) of 4-bromo-2-pyrrolecarboxaldehyde, 950 mg (38.5%) of the expected aldehyde are obtained, with a melting point of 128–9° C.

(b) Ethyl 4-(3,5,5,8,8-pentamethyl-5,6,7,8-tetrahydro-2-naphthyl)-2-pyrroleacrylate In a similar manner to Example 1(d), by reaction of 500 mg (1.7 mmol) of 4-(3,5,5,8,8-pentamethyl-5,6,7,8-tetrahydro-2-naphthyl)-2-pyrrolecarboxaldehyde with 400 µl (2 mmol) of triethyl phosphonoacetate, 570 mg (92%) of the expected ethyl ester are obtained.

(c) 4-(3,5,5,8,8-Pentamethyl-5,6,7,8-tetrahydro-2-naphthyl)-2-pyrroleacrylic acid In a similar manner to Example 1(e), starting with 570 mg (1.9 mmol) of ethyl 4-(3,5,5,8,8-pentamethyl-5,6,7,8-tetrahydro-2-naphthyl)-2-pyrroleacrylate, 240 mg (37%) of 4-(3,5,5,8,8-pentamethyl-5,6,7,8-tetrahydro-2-naphthyl)-2-pyrroleacrylic acid are obtained, with a melting point of 245–6° C.

EXAMPLE 14

3-(3,5,5,8,8-Pentamethyl-5,6,7,8-tetrahydro-2-naphthyl)phenylacrylic acid

In a similar manner to Example 9(b), by reaction of 73.4 g (0.30 mol) of 3,5,5,8,8-pentamethyl-5,6,7,8-tetrahydro-2-naphthylboronic acid with 44.7 g (0.20 mol) of 4-bromophenylacrylic acid, and after recrystallization from ethanol, 48 g (61%) of 3-(3,5,5,8,8-pentamethyl-5,6,7,8-tetrahydro-2-naphthyl)phenylacrylic acid are obtained, with a melting point of 207–8° C.

EXAMPLE 15

3-(5,6,7,8-Tetrahydro-5,5,8,8-tetramethyl-2-naphthyl)phenylpropiolic acid (a) 2',2'-Dibromo-3-(5,6,7,8-tetrahydro-5,5,8,8-tetramethyl-2-naphthyl)phenylethylene In a similar manner to Example 2(a), starting with 2.05 g (7 mmol) of 3-(5,6,7,8-tetrahydro-5,5,8,8-tetramethyl-2-naphthyl)benzaldehyde [prepared in Example 11(a)], 1.07 g (35%) of the expected product are obtained in the form of an oil.

(b) 3-(5,6,7,8-Tetrahydro-5,5,8,8-tetramethyl-2-naphthyl)phenylpropiolic acid 900 mg (2 mmol) of 2',2'-dibromo-3-(5,6,7,8-tetrahydro-5,5,8,8-tetramethyl-2-napthyl)phenyletheylene and 40 ml of THF are introduced into a three-necked flask under a stream of nitrogen. 2.2 ml (5.2 mmol) of n-butyllithium solution (2.5 M in hexane) are added dropwise at −50° C. and the mixture is allowed to return to room temperature. $CO_2$ is introduced at 0° C. for 20 minutes and the mixture is stirred at room temperature for one hour. The reaction medium is poured into saturated ammonium chloride solution and adjusted to pH 1 with hydrochloric acid, the mixture is extracted with ethyl acetate and the organic phase is separated out after settling has taken place, dried over magnesium sulphate and evaporated. The residue obtained is purified by chromatography on a column of silica eluted with a mixture of dichloromethane and methanol (95/5). After evaporation of the solvents, 80 mg (12%) of 3-(5,6,7,8-tetrahydro-5,5,8,8-tetramethyl-2-naphthyl)phenylpropiolic acid are collected, with a melting point of 164–5° C.

EXAMPLE 16

2-Methoxy-5-(3,5,5,8,8-pentamethyl-5,6,7,8-tetrahydro-2-naphthyl)phenylacrylic acid (a) 2-Hydroxy-5-(3,5,5,8,8-pentamethyl-5,6,7,8-tetrahydro-2-naphthyl)benzaldehyde In a similar manner to Example 9(b), by reaction of 15 g (61 mmol) of 3,5,5,8,8-pentamethyl-5,6,7,8-tetrahydro-2-naphthylboronic acid with 8.16 g (41 mmol) of 5-bromo-2-hydroxybenzaldehyde, 11.7 g (89%) of 2-hydroxy-5-(3,5,5,8,8-pentamethyl-5,6,7,8-tetrahydro-2-naphthyl)benzaldehyde are obtained, with a melting point of 138–9° C.

(b) 2-Methoxy-5-(3,5,5,8,8-pentamethyl-5,6,7,8-tetrahydro-2-naphthyl)benzaldehyde In a similar maser to Example 10(b), by reaction of 2 g (6.2 mmol) of 2-hydroxy-5-(3,5,5,8,8-pentamethyl-5,6,7,8-tetrahydro-2-naphthyl)benzaldehyde with 425 μl (6.8 mmol) of iodomethane, 1.68 g (88%) of the expected product are obtained.

(c) Ethyl 2-methoxy-5-(3,5,5,8,8-pentamethyl-5,6,7,8-tetrahydro-2-naphthyl)phenylacrylate In a similar manner to Example 1(d), by reaction of 1.65 g (5 mmol) of 2-methoxy-5-(3,5,5,8,8-pentamethyl-5,6,7,8-tetrahydro-2-naphthyl)benzaldehyde with 1.68 g (7.5 mmol) of triethyl phosphonoacetate, 1.7 g (83%) of the expected ethyl ester are obtained in the form of an oil.

(d) 2-Methoxy-5-(3,5,5,8,8-pentamethyl-5,6,7,8-tetrahydro-2-naphthyl)phenylacrylic acid In a similar maser to Example 1(e), starting with 1.6 g (3.9 mmol) of the above ethyl estser, 1.4 g (93%) of 2-methoxy-5-(3,5,5,8,8-pentamethyl-5,6,7,8-tetrahydro-2-naphthyl)phenylacrylic acid are obtained, with a melting point of 181–2° C.

EXAMPLE 17

2-Propyloxy-5-(3,5,5,8,8-pentamethyl-5,6,7,8-tetrahydro-2-naphthyl)phenylacrylic acid (a) 2-Propyloxy-5-(3,5,5,8,8-pentamethyl-5,6,7,8-tetrahydro-2-naphthyl)benzaldehyde In a similar manner to Example 10(b), by reaction of 2 g (6.2 mmol) of 2-hydroxy-5-(3,5,5,8,8-pentamethyl-5,6,7,8-tetrahydro-2-naphthyl)benzaldehyde [prepared in Example 16(a)] with 670 μl (6.8 mmol) of 1-iodopropane, 2.2 g (88%) of the expected product are obtained in the form of a colourless oil.

(b) Ethyl 2-propyloxy-5-(3,5,5,8,8-pentamethyl-5,6,7,8-tetrahydro-2-naphthyl)phenylacrylate In a similar manner to Example 1(d), by reaction of 2.18 g (6 mmol) of 2-propyloxy-5-(3,5,5,8,8-pentamethyl-5,6,7,8-tetrahydro-2-naphthyl)benzaldehyde with 2.03 g (9 mmol) of triethyl phosphonoacetate, 2.13 g (82%) of the expected ethyl ester are obtained in the form form of a yellow oil.

(c) 2-Propyloxy-5-(3,5,5,8,8-pentamethyl-5,6,7,8-tetrahydro-2-naphthyl)phenylacrylic acid In a similar manner to Example 1(e), starting with 2.1 g (4.8 mmol) of the above ethyl ester, 1.68 g (86%) of 2-propyloxy-5-(3,5,5,8,8-pentamethyl-5,6,7,8-tetrahydro-2-naphthyl)phenylacrylic acid are obtained, with a melting point of 125–6° C.

EXAMPLE 18

2-Heptyloxy-5-(3,5,5,8,8-pentamethyl-5,6,7,8-tetrahydro-2-naphthyl)phenylacrylic acid (a) 2-Heptyloxy-5-(3,5,5,8,8-pentamethyl-5,6,7,8-tetrahydro-2-naphthyl)benzaldehyde In a similar manner to Exmaple 10(b), by reaction of 2 g (9.3 mmol) of 2-hydroxy-5-(3,5,5,8,8-pentamethyl-5,6,7,8-tetrahydro-2-naphthyl)benzaldehyde [prepared in Example 16(a)] with 1.1 ml (6.8 mmol) of 1-bromoheptane, 1.88 g (72%) of the expected product are obtained in the form of a yellow oil.

(b) Ethyl 2-heptyloxy-5-(3,5,5,8,8-pentamethyl-5,6,7,8-tetrahydro-2-naphthyl)phenylacrylate In a similar manner to Example 1(d), by reaction of 1.78 g (4.2 mmol) of 2-heptyloxy-5-(3,5,5,8,8-pentamethyl-5,6,7,8-tetrahydro-2-naphthyl)benzaldehyde with 1.44 g (6.3 mmol) of triethyl phosphonoacetate, 1.89 g (90%) of the expected ethyl ester are obtained in the form of a yellow oil.

(c) 2-Heptyloxy-5-(3,5,5,8,8-pentamethyl-5,6,7,8-tetrahydro-2-naphthyl)phenylacrylic acid In a similar manner to Example 1(e), starting with 1.99 g (3.9 mmol) of the above ethyl ester, 1.2 g (67%) of 2-heptyloxy-5-(3,5,5,8,8-pentamethyl-5,6,7,8-tetrahydro-2-naphthyl)phenylacrylic acid are obtained, with a melting point of 137–8° C.

EXAMPLE 19
2-Methoxymethoxy-5-(3,5,5,8,8-pentamethyl-5,6,7,8-tetrahydro-2-naphthyl)phenylacrylic acid (a) 2-Methoxymethoxy-5-(3,5,5,8,8-pentamethyl-5,6,7,8-tetrahydro-2-naphthyl)benzaldehyde In a similar manner to Example 10(b), by reaction of 3 g (9.3 mmol) of 2-hydroxy-5-(3,5,5,8,8-pentamethyl-5,6,7,8-tetrahydro-2-naphthyl)benzaldehyde [prepared in Example 16(a)] with 777 µl (10.2 mmol) of methoxymethyl chloride, 3.5 g (100%) of the expected product are obtained in the form of an oil.

(b) Ethyl 2-methoxymethoxy-5-(3,5,5,8,8-pentamethyl-5,6,7,8-tetrahydro-2-naphthyl)phenylacrylate In a similar manner to Exmaple 1(d), by reaction of 3.4 g (9.3 mmol) of 2-methoxymethoxy-5-(3,5,5,8,8-pentamethyl-5,6,7,8-tetrahydro-2-naphthyl)benzaldehyde with 4.16 g (18.6 mmol) of triethyl phosphonoacetate, 3.5 g (86%) of the expected ethyl ester are obtained, with a melting point of 100–1° C.

(c) 2-Methoxymethoxy-5-(3,5,5,8,8-pentamethyl-5,6,7,8-tetrahydro-2-naphthyl)phenylacrylic acid In a similar manner to Example 1(e), starting with 1.5 g (3.4 mmol) of the above ethyl ester, 1.2 g (86%) of 2-methoxymethoxy-5-(3,5,5,8,8-pentamethyl-5,6,7,8-tetrahydro-2-naphthyl)phenylacrylic acid are obtained, with a melting point of 191–2° C.

EXAMPLE 20
2-Hydroxy-5-(3,5,5,8,8-pentamethyl-5,6,7,8-tetrahydro-2-naphthyl)phenylacrylic acid (a) Methyl 2-hydroxy-5-(3,5,5,8,8-pentamethyl-5,6,7,8-tetrahydro-2-naphthyl)phenylacrylate 1.9 g (4.35 mmol) of 2-methoxymethoxy-5-(3,5,5,8,8-pentamethyl-5,6,7,8-tetrahydro-2-naphthyl)phenylacrylic acid, 20 ml of methanol and 30 ml of THF are introduced into a round-bottomed flask. 2.8 ml of concentrated sulphuric acid are added and the mixture is stirred at room temperature for 12 hours. The reaction medium is poured into water and extracted with ethyl ether, and the organic phase is. separated out after settling has taken place, washed with water, dried over magnesium sulphate and evaporated. 1.63 g (95%) of methyl 2-hydroxy-5-(3,5,5,8,8-pentamethyl-5,6,7,8-tetrahydro-2-naphthyl)phenylacrylate are collected.

(b) 2-Hydroxy-5-(3,5,5,8,8-pentamethyl-5,6,7,8-tetrahydro-2-naphthyl)phenylacrylic acid In a similar manner to Example 1(e), starting with 1.63 g (4.25 mmol) of the above ethyl ester, 1.3 g (85%) of 2-hydroxy-5-(3,5,5,8,8-pentamethyl-5,6,7,8-tetrahydro-2-naphthyl)phenylacrylic acid are obtained, with a melting point of 204–5° C.

EXAMPLE 21
3-(3-Methoxy-5,6,7,8-tetrahydro-5,5,8,8-tetramethyl-2-naphthyl)phenylacrylic acid (a) 3-Bromo-2-methoxy-5,6,7,8-tetrahydro-5,5,8,8-tetramethylnaphthalene 7 g (24.7 mmol) of 3-bromo-2-hydroxy-5,6,7,8-tetrahydro-5,5,8,6-tetramethylnaphthalene and 40 ml of DMF are introduced into a three-necked flask under a stream of nitrogren. 890mg (29.6 mmol) of sodium hydride (80% in oil) are added portionwise and the mixture is stirred until the evolution of gas has ceased. 1.7 ml (27 mmol) of iodomethane are then added and the mixture is stirred at room temperature for one hour. The reaction medium is poured into water and extracted with ethyl ether, and the organic phase is separated out after settling has taken place, dried over magnesium sulphate and evaporated. 7.3 g (99%) of the expected product are collected in the for of an oil which crystallizes slowly. Melting point 77–8° C.

(b) 2-Methoxy-5,6,7,8-tetrahydro-5,5,8,8-tetramethylnaphthylboronic acid

In a similar manner to Example 3(a), starting with 6.7 g (22.5 mmol) of 3-bromo-2-methoxy-5,6,7,9-tetrahydro-5,5,8,8-tetramethylnaphthalene, 4.54 g (77%) of the expected boronic acid are obtained, with a melting point of 151–2° C.

(c) 3-(3-Methoxy-5,6,7,8-tetrahydro-5,5,8,8-tetramethyl-2-naphthyl)phenylacrylic acid In a similar manner to Example 9(b), by reaction of 2.62 g (10 mmol) of 2-methoxy-5,6,7,8-tetrahydronaphthylboronic acid with 1.51 g (6.7 mmol) of 3-bromophenylacrylic acid, 1.1 g (45%) of 3-(3-methoxy-5,6,7,8-tetrahydro-5,5,8,8-tetramethyl-2-naphthyl)phenylacrylic acid are obtained, with a melting point of 187–8° C.

EXAMPLE 22
3-(3-Propyloxy-5,6,7,8-tetrahydro-5,5,8,8-tetramethyl-2-naphthyl)phenylacrylic acid (a) 3-Bromo-2-propyloxy-5,6,7,8-tetrahydro-5,5,8,8-tetramethylnaphthalene In a similar manner to Example 21(a), by reaction of 7 g (24.7 mmol) of 3-bromo-2-hydroxy-5,6,7,8-tetrahydro-5,5,8,8-tetramethylnaphthalene with 2.45 ml (27 mmol) of 1-bromopropane, 8.1 g (100%) of 3-bromo-2-propyloxy-5,6,7,8-tetrahydro-5,5,8,8-tetramethylnaphthalene are obtained in the form of an orange-coloured oil.

(b) 2-Propyloxy-5,6,7,8-tetrahydro-5,5,8,8-tetramethylnaphthylboronic acid

In a similar manner to Example 3(a), by reaction of 8 g (24.6 mmol) of 3-bromo-2-propyloxy-5,6,7,8-tetrahydro-5,5,8,8-tetramethylnaphthalene, 5.7 g (80%) of the expected boronic acid are obtained, with a melting point of 138–9° C.

(c) 3-(3-Propyloxy-5,6,7,8-tetrahydro-5,5,8,8-tetramethyl-2-naphthyl)phenylacrylic acid In a similar manner to Example 9(b), by reaction of 5 g (17.2 mmol) of 2-propyloxy-5,6,7,8-tetrahydro-5,5,8,8-tetramethylnaphthylboronic acid with 2.6 g (11.5 mmol) of 3-bromophenylacrylic acid, 1.66 g (35%) of 3-(3-propyloxy-5,6,7,8-tetrahydro-5,5,8,8-tetramethyl-2-naphthyl)phenylacrylic acid are obtained, with a melting point of 172–3° C.

EXAMPLE 23
3-(3-Heptyloxy-5,6,7,8-tetrahydro-5,5,8,8-tetramethyl-2-naphthyl)phenylacrylic acid (a) 3-Bromo-2-heptyloxy-5,6,7,8-tetrahydro-5,5,8,8-tetramethylnaphthalene In a similar manner to Example 21(a), by reaction of 7 g (24.7 mmol) of 3-bromo-2-hydroxy-5,6,7,8-tetrahydro-5,5,8,8-tetramethylnaphthalene with 4.24 ml (27 mmol) of 1-bromoheptane, 10 g (100%) of 3-bromo-2-heptyloxy-5,6,7,8-tetrahydro-5,5,8,8-tetramethylnaphthalene are obtained in the form of a brown oil.

(b) 2-Heptyloxy-5,6,7,8-tetrahydro-5,5,8,8-tetramethylnaphthylboronic acid

In a similar manner to Example 3(a), starting with 10 g (26.2 mmol) of 3-bromo-2-heptyloxy-5,6,7,8-tetrahydro-5,5,8,8-tetramethylnaphthalene, 6.1 g (67%) of the expected boronic acid are obtained, with a melting point of 102–3° C.

(c) 3-(3-Heptyloxy-5,6,7,8-tetrahydro-5,5,8,8-tetramethyl-2-naphthyl)phenylacrylic acid In a similar manner to Example 9(b), by reaction of 5 g (14.4 mmol) of 2-heptyloxy-5,6,7,8-tetrahydro-5,5,8,8-tetramethylnaphthylboronic acid with 2.52 g (11.1 mmol) of 3-bromophenylacrylic acid, 2.7 g (54%) of 3-(3-heptyloxy- 5,6,7,8-tetrahydro-5,5,8,8-tetramethyl-2-naphthyl)phenylacrylic acid are obtained, with a melting point of 112–3° C.

EXAMPLE 24
3-(3-Methoxymethoxy-5,6,7,8-tetrahydro-5,5,8,8-tetramethyl-2-naphthyl)phenylacrylic acid (a) 3-Bromo-2-methoxymethoxy-5,6,7,8-tetrahydro-5,5,8,8-tetramethylnaphthalene In a similar manner to Example 21(a), by reaction of 7 g (24.7 mmol) of 3-bromo-2-hydroxy-5,6,7,8-tetrahydro-5,5,8,8-tetramethylnaphthalene with 2.05 ml (27 mmol) of methoxymethyl chloride, 8.1 g (100%) of 3-bromo-2-methoxymethoxy-5,6,7,8-tetrahydro-5,5,8,8-tetramethylnaphthalene are obtained in the form of a light-brown oil.

(b) 2-Methoxymethoxy-5,6,7,8-tetrahydro-5,5,8,8-tetramethylnaphthylboronic acid

In a similar manner to Example 3(a), starting with 8 g (24.4 mmol) of 3-bromo-2-methoxymethoxy-5,6,7,8-tetrahydro-5,5,8,8-tetramethylnaphthalene, 5.5 g (77%) of the expected boronic acid are obtained, with a melting point of 133–4° C.

(c) 3-(3-Methoxymethoxy-5,6,7,8-tetrahydro-5,5,8,8-tetramethyl-2-naphthyl)phenylacrylic acid In a similar manner to Example 9(b), by reaction of 5.3 g (18.1 mmol) of 2-methoxymethoxy-5,6,7,8-tetrahydro-5,5,8,8-tetramethylnaphthylboronic acid with 3.16 g (14 mmol) of 3-bromophenylacrylic acid, 4.39 g (80%) of 3-(3-methoxymethoxy-5,6,7,8-tetrahydro-5,5,8,8-tetramethyl-2-naphthyl)phenylacrylic acid are obtained, with a melting point of 156–7° C.

EXAMPLE 25
3-(3-Hydroxy-5,6,7,8-tetrahydro-5,5,8,8-tetramethyl-2-naphthyl)phenylacrylic acid (a) Methyl 3-(3-hydroxy-5,6,7,8-tetrahydro-5,5,8,8-tetramethyl-2-naphthyl)phenylacrylate 2 g (5 mmol) of 3-(3-methoxymethoxy-5,6,7,8-tetrahydro-5,5,8,8-tetramethyl-2-naphthyl)phenylacrylic acid, 10 ml of methanol and 10 ml of THF are introduced into a round-bottomed flask. 2.8 ml of concentrated sulphuric acid are added and the mixture is stirred at room temperature for &é hours. The reaction medium is poured into water and extracted with ethyl ether, and the organic phase is separated out after settling has taken place, washed with water, dried over magnesium sulphate and evaporated. 1.80 g (98%) of the expected methyl ester are collected, with a melting point of 182–3° C.

(b) 3-(3-Hydroxy-5,6,7,8-tetrahydro-5,5,8,8-tetramethyl-2-naphthyl)phenylacrylic acid In a similar manner to Example 1(e), starting with 1.5 g (4.1 mmol) of the above methyl ester, 1.3 g (90%) of 3-(3-hydroxy-5,6,7,8-tetrahydro-5,5,8,8-tetramethyl-2-naphthyl)phenylacrylic acid are obtained, with a melting point of 244–5° C.

EXAMPLE 26
3-(4,4,7-Trimethylthiochroman-6-yl)phenylacrylic acid (a) 1-Methyl-3-(3-methylbut-2-enyl)sulphanylbenzene 5 g (40 mmol) of 3-methylthiophenol, 5.6 g (40 mmol) of potassium carbonate and 50 ml of DMF are introduced into a three-necked flask. 7.2 g (48 mmol) of 3-methyl-2-butene bromide are added and the mixture is stirred at room temperature for four hours. The reaction medium is poured into water and extracted with ethyl ether, and the organic phase is separated out after settling has taken place, dried over magnesium sulphate and evaporated. 7.8 g (100%) of the expected product are collected in the form of a yellow oil.

(b) 4,4,7-Trimethylthiochroman 7 g (36.4 mmol) of 1-methyl-3-(3-methylbut-2-enyl)sulphanylbenzene and 50 ml of toluene are introduced into a round-bottomed flask and 10.4 g (54.6 mmol) of para-toluenesulphonic acid are added. The mixture in refluxed for four hours. The reaction medium is evaporated to dryness, the residue is taken up in water and ethyl ether and the organic phase is separated out after settling has taken place, dried over magnesium sulphate and evaporated. 6.8 g (97%) of the thiochroman are collected in the form of a brown oil.

(c) 6-Bromo-4,4,7-trimethylthiochroman 6.2 g (32.2 mmol) of 4,4,7-trimethylthiochroman, 40 ml of dichloromethane and 90 mg of iron powder are introduced into a three-necked flask. 1.65 ml (32.2 mmol) of bromine are added and the mixture is stirred at room temperature for two hours. The reaction medium is poured into sodium bicarbonate solution and extracted with dichloromethane, and the organic phase is separated out after settling has taken place, dried over magnesium sulphate and evaporated. The residue obtained is purified by chromatography on a column of silica eluted with heptane. 5.9 g (67%) of the bromo derivative are collected in the form of a pale yellow oil.

(d) 4,4,7-Trimethylthiochromanylboronic acid

In a similar manner to Example 3(a), starting with 5.8 g (21.4 mmol) of 6-bromo-4,4,7-trimethylthiochroman, 3.88 g (76%) of the expected boronic acid are obtained, with a melting point of 252–3° C.

(e) 3-(4,4,7-Trimethylthiochroman-6-yl)phenylacrylic acid

In a similar manner to Example 9(b), by reaction of 1.5 g (6.3 mmol) of 4,4,7-trimethylthiochromanylboronic acid with 1.2 g (5.3 mmol) of 3-bromophenylacrylic acid, 1.1 g (99%) of 3-(4,4,7-trimethylthiochroman-6-yl)phenylacrylic acid are obtained, with a melting point of 102–3° C.

EXAMPLE 27
N-Ethyl-3-(3,5,5,8,8-pentamethyl-5,6,7,8-tetrahydro-2-naphthyl)phenylacrylamide (a) 3-(3,5,5,8,8-Pentamethyl-5,6,7,8-tetrahydro-2-naphthyl)phenylacryloyl chloride 3.5 g (10 mmol) of 3-(3,5,5,8,8-pentamethyl-5,6,7,8-tetrahydro-2-naphthyl)phenylacrylic acid and 50 ml of dichloromethane are introduced into a round-bottomed flask and 2 ml (10 mmol) of dicylcohexylamine are added. The mixture is stirred at room temperature for 10 minutes and 729 µl (10 mmol) of thionyl chloride are then introduced with stirring for 15 minutes. The reaction medium is evaporated to dryness, the residue is taken up in ethyl ether, the dicyclohexylamine salt is filtered off and the filtrate is evaporated. 3.7 g (100%) of the crude acid chloride are collected, which will be used in its current state for the rest of the synthesis.

(b) N-Ethyl-3-(3,5,5,8,8-pentamethyl-5,6,7,8-tetrahydro-2-naphthyl)phenylacrylamide 20 ml of THF are introduced into a round-bottomed flask and 2.8 ml (35 mmol) of ethylamine solution (70%) are added. A solution of 1.2 g (3.2 mmol) of 3-(3,5,5,8,8-pentamethyl-5,6,7,8-tetrahydro-2-naphthyl)phenylacryloyl chloride in 40 ml of THF is added dropwise and the mixture is stirred at room temperature for one hour. The reaction medium is acidified with hydrochloric acid and extracted with ethyl ether, and the organic phase is separated out after settling has taken place, dried over magnesium sulphate and evaporated. The residue obtained is purified by chromatography on a column of silica eluted with dichloromethane. After evaporation of the solvents, 817 mg (68%) of N-ethyl-3-(3,5,5,8,8-pentamethyl-5,6,7,8-tetrahydro-2-naphthyl)-phenylacrylamide are collected, with a melting point of 158–9° C.

EXAMPLE 28

N-(4-Hydroxyphenyl)-3-(3,5,5,8,8-pentamethyl-5,6,7,8-tetrahydro-2-naphthyl)phenylacrylamide In similar manner to Example 27(a), by reaction of 1.2 g (3.2 mmol) of 3-(3,5,5,8,8-pentamethyl-5,6,7,8-tetrahydro-2-naphthyl)phenylacryloyl chloride with 349 mg (3.2 mmol) of 4-hydroxyaniline, 810 mg of (57%) of N-(4-hydroxyphenyl)-3-(3,5,5,8,8-pentamethyl-5,6,7,6-tetrahydro-2-naphthyl)phenylacrylamide are obtained, with a melting point of 240–1° C.

EXAMPLE 29

3-(3,5,5,8,8-Pentamethyl-5,6,7,8-tetrahydro-2-naphthyl)phenylacrylic acid morpholide In a similar manner to Example 27(a), by reaction of 1.3 g (3.4 mol) of 3-(3,5,5,8,8-pentamethyl-5,6,7,8-tetrahydro-2-naphthyl)phenylacryloyl chloride with 620 µl of (7.12 mmol) of morpholine, 1.25 g (88%) of 3-(3,5,5,8,8-pentamethyl-5,6,7,8-tetrahydro-2-naphthyl)phenylacrylic acid morpholide are obtained, with a melting point of 158–9° C.

EXAMPLE 30

Ethyl 3-(3,5,5,8,8-pentamethyl-5,6,7,8-tetrahydro-2-naphthyl)phenylacrylate

In a similar manner to Example 1(d), by reaction of 5 g (16.3 mmol) of 3-(3,5,5,8,8-pentamethyl-5,6,7,8-tetrahydro-2-naphthyl)benzaldehyde with 4.79 g (21.2 mmol) of triethyl phosphonoacetate, 5 g (81%) of ethyl 3-(3,5,5,8,8-pentamethyl-5,6,7,8-tetrahydro-2-naphthyl)phenylacrylate are obtained, with a melting point of 70–2° C.

EXAMPLE 31

3-[3-(3.5,5,8,8-Pentamethyl-5,6,7,8-tetrahydro-2-naphthyl)phenyl]but-2-enoic acid (a) 3-(3,5,5,8,8-Pentamethyl-5,6,7,8-tetrahydro-2-naphthyl) acetophenone In a similar manner to Example 9(b), by reaction of 5 g (20.3 mmol) of 3,5,5,8,8-pentamethyl-5,6,7,8-tetrahydro-2-naphthylboronic acid with 2.7 g (13.5 mmol) of 3-bromoacetophenone, 4.3 g (90%) of the expected product are obtained, with a melting point of 89–90° C.

(b) Ethyl 3-[3-(3,5,5,8,8-pentamethyl-5,6,7,8-tetrahydro-2-naphthyl)phenyl]but-2-enoate In a similar manner to Example 1(d), by reaction of 3.7 g (11.5 mmol) of 3-(3,5,5,8,8-pentamethyl-5,6,7,8-tetrahydro-2-naphthyl)acetophenone with 3.9 g (17.3 mmol) of triethyl phosphonoacetate, 2.67 g (60%) of the expected ethyl ester are obtained in the form of a yellow oil.

(c) 3-[3-(3,5,5,8,8-Pentamethyl-5,6,7,8-tetrahydro-2-naphthyl)phenyl]but-2-enoic acid In a similar manner to Example 1(e), starting with 2.5 g (6.4 mmol) of the above ethyl ester, 1.63 g (70%) of 3-[3-(3,5,5,8,8-pentamethyl-5,6,7,8-tetrahydro-2-naphthyl)phenyl]but-2-enoic acid are obtained, with a melting point of 166–7° C.

EXAMPLE 32

Various solid formulations based on compounds according to the invention are illustrated in this example.

A - ORAL ROUTE (a) 0.2 g tablet

| | |
|---|---|
| Compound of Example 1 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Drinkable suspension in 5 ml ampoules

| | |
|---|---|
| Compound of Example 3 | 0.001 g |
| Glycerol | 0.500 g |
| 70% Sorbitol | 0.500 g |
| Sodium saccharinate | 0.010 g |
| Methyl para-hydroxybenzoate | 0.040 g |
| Flavouring | qs |
| Purified water | qs 5 ml |

(c) 0.8 g tablet

| | |
|---|---|
| Compound of Example 5 | 0.500 g |
| Pregelatinized starch | 0.100 g |
| Microcrystalline cellulose | 0.115 g |
| Lactose | 0.075 g |
| Magnesium stearate | 0.010 g |

(d) Drinkable suspension in 10 ml ampoules

| | |
|---|---|
| Compound of Example 2 | 0.050 g |
| Glycerol | 1.000 g |
| 70% Sorbitol | 1.000 g |
| Sodium saccharinate | 0.010 g |
| Methyl para-hydroxybenzoate | 0.080 g |
| Flavouring | qs |
| Purified water | qs 10 ml |

B - TOPICAL ROUTE (a) Ointment

| | |
|---|---|
| Compound of Example 21 | 0.020 g |
| Isopropyl myristate | 81.700 g |
| Liquid petroleum jelly | 9.100 g |
| Silica ("Aerosil 200" sold by Degussa) | 9.180 g |

(b) Ointment

| | |
|---|---|
| Compound of Example 9 | 0.300 g |
| White petroleum jelly codex | qs 100 g |

(c) Nonionic water-in-oil cream

| | |
|---|---|
| Compound of Example 7 | 0.100 g |
| Mixture of emulsifying lanolin alcohols, waxes and oils ("Anhydrous Eucerin" sold by BDF) | 39.900 g |
| Methyl para-hydroxybenzoate | 0.075 g |
| Propyl para-hydroxybenzoate | 0.075 g |
| Sterile demineralized water | qs 100 g |

(d) Lotion

| | |
|---|---|
| Compound of Example 30 | 0.100 g |
| Polyethylene glycol (PEG 400) | 69.900 g |
| 95% Ethanol | 30.000 g |

(e) Hydrophobic ointment

| | |
|---|---|
| Compound of Example 25 | 0.300 g |
| Isopropyl myristate | 36.400 g |
| Silicone oil ("Rhodorsil 47 V 300" sold by Rhône-Poulenc) | 36.400 g |
| Beeswax | 13.600 g |
| Silicone ("Abil 300,000 cst" sold by Goldschmidt) | qs 100 g |

(f) Nonionic oil-in-water cream

| | |
|---|---|
| Compound of Example 14 | 0.500 g |
| Cetyl alcohol | 4.000 g |
| Glyceryl monostearate | 2.500 g |
| PEG 50 stearate | 2.500 g |
| Karite butter | 9.200 g |

| | |
|---|---|
| -continued | |
| Propylene glycol | 2.000 g |
| Methyl para-hydroxybenzoate | 0.075 g |
| Propyl para-hydroxybenzoate | 0.075 g |
| Sterile demineralized water | qs 100 g |

What is claimed is:

1. A bicyclic aromatic compound, having the general formula (I):

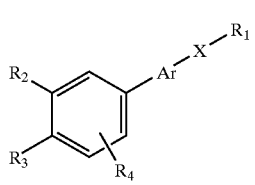

wherein, $R_1$ represents:
   (i) the —$CH_3$ radical;
   (ii) the radical —$CH_2OR_5$; or
   (iii) the radical —$COR_6$;

Ar is a radical of the formula (c) or (d):

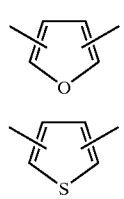

X represents

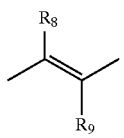

or

$R_2$ and $R_3$, which may be identical or different, represent
   (i) a hydrogen atom;
   (ii) an alkyl radical having at least 3 carbon atoms, among which the carbon attached to the phenyl radical is substituted with at least two carbon atoms;
   (iii) a radical —$OR_5$;
   (iv) a radical —$SR_5$; or $R_2$ and $R_3$, taken together, form with the adjacent aromatic ring a 5- or 6-membered ring optionally substituted with methyl groups and/or optionally interrupted by an oxygen or sulphur atom, with the proviso that:
$R_2$ and $R_3$ cannot both be hydrogen;
$R_2$ and $R_3$ cannot both be a radical —$OR_5$;
$R_2$ and $R_3$ cannot both be a radical —$SR_5$;
when $R_2$ is hydrogen, $R_3$ cannot be a radical —$OR_5$ or a radical —$SR_5$;
when $R_2$ is a radical —$OR_5$, $R_3$ cannot be hydrogen or a radical —$SR_5$;
when $R_2$ is a radical —$SR_5$, $R_3$ cannot be a radical —$OR_5$ or hydrogen;
when $R_3$ is hydrogen, $R_2$ cannot be a radical —$OR_5$ or a radical —$SR_5$;
when $R_3$ is a radical —$OR_5$, $R_2$ cannot be hydrogen or a radical —$SR_5$;
when $R_3$ is a radical —$SR_5$, $R_2$ cannot be a radical —$OR_5$ or hydrogen;

$R_4$ and $R_7$, which may be identical or different, represent a hydrogen atom, a halogen atom, a linear or branched alkyl radical having from 1 to 20 carbon atoms or a radical —$OR_5$, $R_5$ represents a hydrogen atom, a lower alkyl radical or a radical —$COR_{10}$ $R_6$ represents:
   (a) a hydrogen atom;
   (b) a lower alkyl radical;
   (c) a radical of formula:

or (d) a radical —$OR_{11}$ $R_8$ and $R_9$, which may be identical or different, represent a hydrogen atom or a lower alkyl radical, $R_{10}$ represents a lower alkyl radical, $R_{11}$ represents a hydrogen atom, a linear or branched alkyl radical having from 1 to 20 carbon atoms, and alkenyl radical, a mono- or polyhydroxyalkyl radical, an optionally substituted aryl or aralkyl radical, a sugar residue or an amino acid or peptide residue, R' and R", which may be identical or different, represent a hydrogen atom, a lower alkyl radical, a mono- or polyhydroxyalkyl radical, an optionally substituted aryl radical or an amino acid or sugar residue, or alternatively, taken together form a heterocycle, a salt thereof or an optical or geometrical isomer thereof.

2. A compound according to claim 1, selected from the group consisting of alkali metals, alkaline-earth metals, zinc salts and organic amine salts.

3. A compound according to claim 1, selected from the group consisting of:

5-(3-tert-butyl-4-methoxyphenyl)-2-thiopheneacrylic acid,
5-(3-tert-butyl-4-methoxyphenyl)-2-thiophenpropiolic acid,
2-(3-tert-butyl-4-methoxyphenyl)-4-thiopheneacrylic acid,
4-(3-tert-butyl-4-methoxyphenyl)-2-thiopheneacrylic acid,
5-(3,5,5,8,8-pentamethyl-5,6,7,8-tetrahydro-2-naphthyl)-2-thiopheneacrylic acid,
4-(3,5,5,8,8-pentamethyl-5,6,7,8-tetrahydro-2-naphthyl)-2-thiopheneacrylic acid,
4-(5-6,7,8-tetrahydro-5,5,8,8-tetramethyl-2-naphthyl)-2-thiopheneacrylic acid, and
5-(3,5,5,8,8-pentamethyl-5,6,7,8-tetrahydro-2-naphthyl)-2-thiophenepropiolic acid.

4. A compound according to claim 1, having at least one of the following groups:

$R_1$ represents the radical —$COR_6$;

Ar represents a radical of formula (d);

X represents the radical:

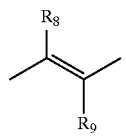

or

R$_2$ and R$_3$, taken together, form with the adjacent aromatic ring a 5- or 6-membered ring, optionally substituted with methyl groups and/or optionally interrupted by an oxygen or sulfur atom.

5. A compound according to claim 1, wherein Ar is a radical of formula (d).

6. A pharmaceutical composition comprising at least one compound according to claim 1 in a pharmaceutically acceptable support.

7. The composition of claim 6, wherein the concentration of the at least one compound is between 0.002% and 5% by weight of the pharmaceutical composition.

8. A cosmetic composition comprising at least one compound according to claim 1 in a cosmetically acceptable support.

9. The composition of claim 8, wherein the concentration of the at least one compound is between 0.002% and 5% by weight of the cosmetic composition.

10. The composition of claim 8, wherein the composition is suitable for body or hair hygiene.

11. A compound according to claim 1, wherein R$_2$ and R$_3$, taken together form with the adjacent aromatic ring a 6-membered ring substituted with methyl groups and being interrupted by an oxygen or sulfur atom.

12. A compound according to claim 1, wherein R' and R" taken together form a heterocycle.

* * * * *